United States Patent [19]

Ogawa et al.

[11] Patent Number: 5,532,273
[45] Date of Patent: Jul. 2, 1996

[54] METHOD FOR CONTROLLING PINK BOLLWORM THROUGH DISTURBANCE OF MALE-FEMALE COMMUNICATION THEREOF

[75] Inventors: Kinya Ogawa; Tetsuo Kitagaki, both of Kanagawa; Akira Yamamoto, Niigata, all of Japan

[73] Assignee: Shin-Etsu Chemical Co., Ltd., Tokyo, Japan

[21] Appl. No.: 469,792

[22] Filed: Jun. 6, 1995

Related U.S. Application Data

[63] Continuation of Ser. No. 40,220, Apr. 1, 1993, abandoned.

[30] Foreign Application Priority Data

Aug. 19, 1992 [JP] Japan .................... 4-219528

[51] Int. Cl.$^6$ .................... A01N 25/00; A01N 37/00; A01N 31/02
[52] U.S. Cl. .................... 514/546; 514/739; 424/84; 424/405; 424/408
[58] Field of Search .................... 514/546, 549, 514/739, 724; 424/84, 405, 408; 43/58, 107

[56] References Cited

U.S. PATENT DOCUMENTS

| | | | |
|---|---|---|---|
| 3,996,270 | 12/1976 | Friedman et al. | 424/84 |
| 4,600,146 | 7/1986 | Ohno | 239/6 |
| 4,923,119 | 5/1990 | Yamamoto et al. | 424/84 |
| 4,929,441 | 5/1990 | Flint et al. | 424/84 |
| 5,236,715 | 8/1993 | McDonough et al. | 424/84 |

OTHER PUBLICATIONS

Chemical Abstracts 98:197818a (1983); abstracting Lin et al. "Synthesis of the pheromone of the pink bollworm . . ." Chem. Nat. Prod., Proc. Sino–Am. Symp., published 1982, pp. 162–167.

Chemical Abstracts 95:203268C (1981); abstracting Lin et al. "Synthesis and Determination of the isomeric ratio of the sex pheromone of the pink bollworm moth" Yu Chi Hua Hsueh, vol. 4, 1981, pp. 273–279.

Lin et al., "Synthesis of the sex pheromone of the pink bollworm . . ." Chem. Nat. Prod., Proc. Sino–Am. Sym. 1980, published 1982, pp. 162–167.

Lin et al., "Synthesis and Determination of the isomeric ratio of the sex pheromone of the pink bollworm moth," Yu Chi Hua Hsueh, 1981, vol. 4, pp. 273–279.

*Primary Examiner*—Allen J. Robinson
*Assistant Examiner*—John D. Pak
*Attorney, Agent, or Firm*—McAulay Fisher Nissen Goldberg & Kiel

[57] ABSTRACT

A control composition which comprises Z,Z/Z,E-7,11-hexadecadienyl acetate and Z,Z/Z,E-7,11-hexadecadienyl alcohol is released into a cotton field in a weight ratio of Z,Z/Z,E-7,11-hexadecadienyl acetate to Z,Z/Z,E-7,11-hexadecadienyl alcohol ranging from 99.2:0.8 to 90:10. The control composition is preferably released in the weight ratio defined above and in a rate ranging from 4 to 80 mg/hr/hectare of field.

7 Claims, 2 Drawing Sheets

METHOD FOR CONTROLLING PINK BOLLWORM THROUGH DISTURBANCE OF MALE-FEMALE COMMUNICATION THEREOF

This is a continuation of application Ser. No. 08/040,220, filed Apr. 1, 1993, which is now abandoned.

BACKGROUND OF THE INVENTION

The present invention relates to a method for controlling pink bollworm by mating disruption of the pink bollworm to thus control the proliferation thereof.

Pink bollworm is a harmful insect which inflicts serious damage to the cotton plant and the control thereof has been a worldwide problem. There have been proposed techniques for controlling the insect by mating disruption of the imagines thereof (disturbance of any male-female communication) by the use of the sex pheromone of the pink bollworm or analog thereof. For instance, Environ. Entomol., 1, p. 645 discloses a method which makes use of Z-7-hexadecenyl acetate as an effective component and Science, 196, p. 904 discloses a method which makes use of gossyplure (a 1:1 mixture of Z,Z-7,11-hexadecadienyl acetate and Z,E-7,11-hexadecadienyl acetate), which is the sex pheromone of the pink bollworm, as an effective component. These effective components are very expensive and, therefore, there has been desired for the development of a control composition which is highly effective for disturbing the male-female communication of the insects in a small amount.

A control composition which can satisfy such requirements comprises the mixture of sex pheromone and an attraction-inhibitory substance. Upon practical use of the control composition, the composition loaded in a polyethylene tube is applied in a cotton field and thus the effective components are gradually allowed to emit into the air through the wall of the polyethylene tube. More specifically, this control composition is an agent used in the form of a sustained release formulation provided with a barrier layer.

However, the sex pheromone and the attraction-inhibitory substance in the control composition are not always released in proportion to the predetermined mixing ratio. The sex pheromone and the attraction-inhibitory substance are different from one another and, therefore, the vapor pressures thereof are also different. However, the difference between the vapor pressures of these compounds is very small since the former is an acetate derivative of an unsaturated aliphatic compound and the latter is an alcohol derivative of the same unsaturated aliphatic compound. For this reason, it is difficult to consider that the variation in the rate of release is ascribed to the difference in the vapor pressure. In fact, if the control composition is allowed to emit into the air without using any barrier layer, it has been confirmed that the sex pheromone and the attraction-inhibitory substance in the control composition are approximately released in proportion to the predetermined mixing ratio. Under such circumstances, the inventors of this invention have conducted various studies and have found out that the sex pheromone and the attraction-inhibitory substance in the control composition are not always released in proportion to the predetermined mixing ratio since they are not always allowed to emit through the barrier layer at the same rates.

For instance, when a control composition which comprises 100 parts by weight of a sex pheromone, i.e., Z,Z/Z, E-7,11-hexadecadienyl acetate (a mixture of Z,Z-7,11-hexadecadienyl acetate and Z,E-7,11-hexadecadienyl acetate; the same expression will be used hereinafter) and one part by weight of an attraction-inhibitory substance, i.e., Z,Z/Z,E-7,11-hexadecadienyl alcohol (a mixture of Z,Z-7,11-hexadecadienyl alcohol and Z,E-7,11-hexadecadienyl alcohol; the same expression will be used hereinafter) is loaded in a polyethylene tube and the resulting formulation is used for releasing these components into the air, the composition released into the air through the polyethylene barrier comprises 100 parts by weight of Z,Z/Z,E-7,11-hexadecadienyl acetate and 0.5 part by weight of Z,Z/Z,E- 7,11-hexadecadienyl alcohol. For this reason, the composition does not ensure sufficient control effect. In particular, when the population of the pink bollworm is high, the control effect of the composition through disturbance of the male-female communication is not sufficient.

SUMMARY OF THE INVENTION

An object of the present invention is to solve the foregoing problems associated with the conventional control composition for pink bollworm and more specifically to provide a method for controlling pink bollworm by mating disruption, which can ensure a satisfactory control effect.

The foregoing object of the present invention can effectively be accomplished by providing a method for controlling pink bollworm through disturbance of the male-female communication thereof which comprises allowing to emit a sex pheromone: Z,Z/Z,E-7,11-hexadecadienyl acetate and an attraction-inhibitory substance: Z,Z/Z,E- 7,11-hexadecadienyl alcohol in a weight ratio ranging from 99.2:0.8 to 90:10.

According to the method for controlling pink bollworm through disturbance of the male-female communication thereof, a sufficiently high communication-disturbing effect can be ensured even in an amount of the effective components smaller than that required for the conventional method for controlling the insect through disturbance of communication and the method of this invention is accordingly quite economical. The control of pink bollworm by mating disruption has conventionally been considered to be difficult when the population thereof is high, but the method of the present invention can ensure a sufficient control effect even in such case.

DETAILED EXPLANATION OF THE INVENTION

Figure 1:
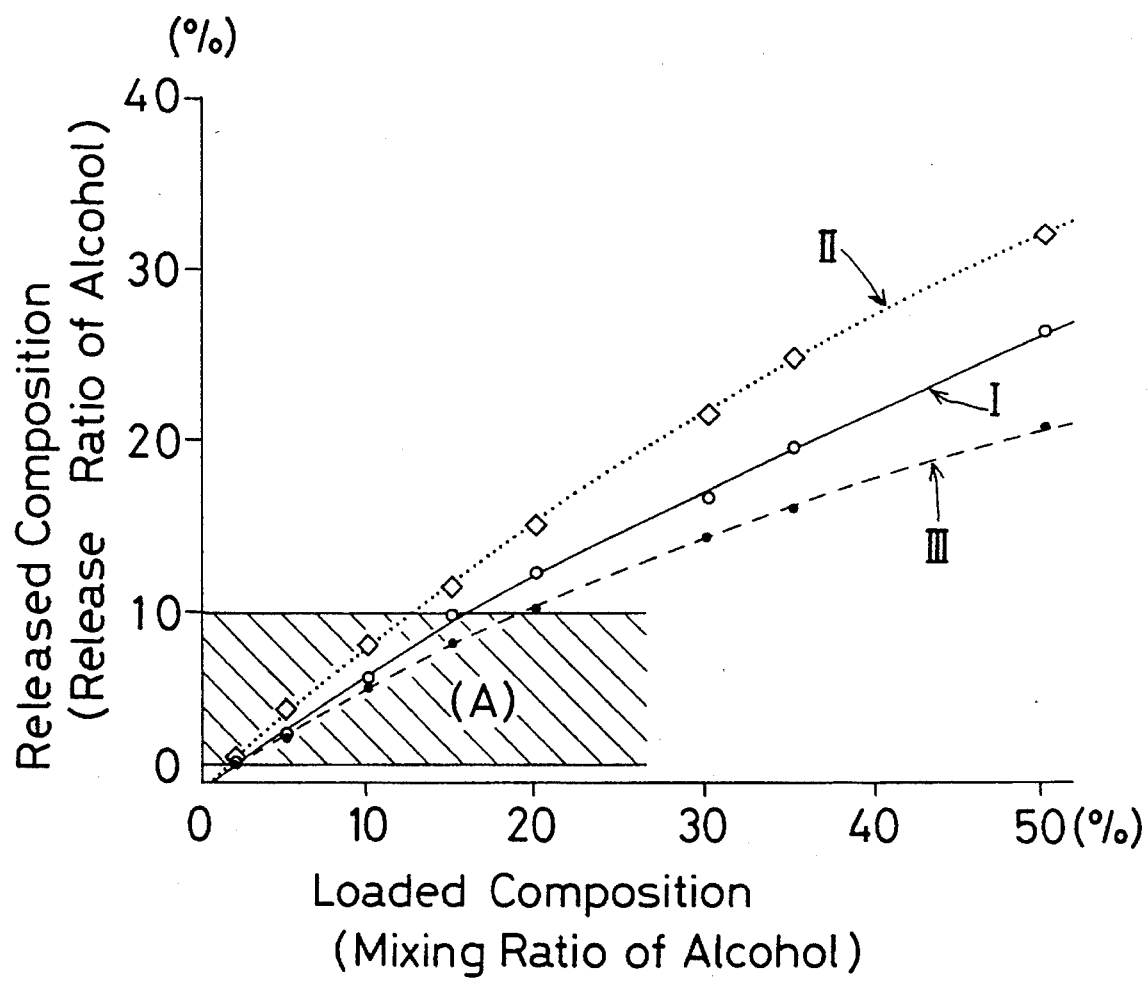
FIG. 1 is a graph showing a relationship between the loaded composition and the released composition.

The method for controlling pink bollworm according to the present invention comprises the step of allowing to emit a sex pheromone: Z,Z/Z,E-7,11-hexadecadienyl acetate and an attraction-inhibitory substance: Z,Z/Z,E-7,11-hexadecadienyl alcohol into the air (or cotton field) in a weight ratio ranging from 99.2:0.8 to 90:10. It is more preferred to release these components in a weight ratio ranging from 98.7:1.3 to 95:5. This is because if the weight ratio of Z,Z/Z,E-7,11-hexadecadienyl alcohol to Z,Z/Z,E-7,11-hexadecadienyl acetate released into the air is less than 0.8/99.2, or more than 10/90, a desired communication-disturbing effect cannot be anticipated.

Both the ratio of Z,Z-7,11-hexadecadienyl acetate to Z,E-7,11-hexadecadienyl acetate (Z,Z:Z,E) present in the sex pheromone (Z,Z/Z,E-7,11-hexadecadienyl acetate) and the ratio of Z,Z-7,11-hexadecadienyl alcohol to Z,E-7,11-hexadecadienyl alcohol (Z,Z:Z,E) present in the attraction-inhibitory substance (Z,Z/Z,E-7,11-hexadecadienyl alcohol) desirably range from 3:7 to 7:3 since the communication-disturbing effect of the resulting control composition is insufficient if the ratios are beyond the range defined above.

The control composition comprising Z,Z/Z,E-7,11-hexadecadienyl acetate and Z,Z/Z,E-7,11-hexadecadienyl alcohol in the weight ratio defined above is preferably released in a rate of 4 to 80 mg/hr/hectare of cotton field. This is because, if it is less than 4 mg/hr/hectare of cotton field, a desired communication-disturbing effect cannot be ensured. Moreover, a sufficient communication-disturbing effect can be anticipated when it is used in an amount of 80 mg/hr/hectare of cotton field, for almost all of the conditions of location for cotton fields. Therefore, the use thereof in an amount more than 80 mg/hr/hectare of cotton field is fruitless and unfavorable from the economical viewpoint.

The control composition comprising Z,Z/Z,E-7,11-hexadecadienyl acetate and Z,Z/Z,E-7,11-hexadecadienyl alcohol can be loaded in a plastic film and applied in a cotton field to thus adjust the release ratio and released amount to the levels defined above. As has been explained above, the control composition is preferably used in the form of a sustained release formulation provided with a barrier layer.

When the control composition is loaded in a plastic film to give a sustained release formulation, the weight ratio of Z,Z/Z,E-7,11-hexadecadienyl alcohol to Z,Z/Z,E-7,11-hexadecadienyl acetate must be greater than the release weight ratio defined above. The rate of Z,Z/Z,E-7,11-hexadecadienyl acetate released into the circumstances through the barrier layer (a plastic film) differs from and is higher than the rate of Z,Z/Z,E-7,11-hexadecadienyl alcohol released into the circumstances through the barrier layer and, therefore, the relative amount of the former is increased to thus accomplish the predetermined release ratio.

The release ratio of Z,Z/Z,E-7,11-hexadecadienyl alcohol to Z,Z/Z,E-7,11-hexadecadienyl acetate can be determined through the analysis of the released vapor from the loaded control composition by the gas chromatography technique.

Preferably, the plastic film serving as a barrier layer may be, for instance, a polyethylene, polypropylene or ethylene-vinyl acetate copolymer. In addition, the thickness of the plastic film preferably ranges from 200 to 800 μm. The emission rates of Z,Z/Z,E-7,11-hexadecadienyl acetate and Z,Z/Z,E-7,11-hexadecadienyl alcohol through the plastic film vary depending on the kinds and thicknesses of the plastic films used and, therefore, an appropriate mixing weight ratio of these ingredients should be adjusted depending on the kind and thickness of the plastic film used. If the plastic films listed above are used, the emission rate of Z,Z/Z,E-7,11-hexadecadienyl acetate through the plastic film is higher than that of Z,Z/Z,E-7,11-hexadecadienyl alcohol and thus, the relative amount of the latter should be increased.

The figure of the sustained release formulation of the control composition prepared by loading the composition in a plastic film is not restricted to a specific one. For instance, the sustained release formulation can be prepared by introducing the control composition into a tube of a small diameter and then sealing the tube; or by loading the composition in a bag of a laminate film and then sealing the bag; or sealing the composition in a capsule or an ampoule.

The method for controlling pink bollworm through the disturbance of male-female communication thereof according to the present invention will hereinafter be explained in more detail with reference to the following non-limitative working Examples.

The following experiments were carried out to examine the weight ratio of Z,Z/Z,E-7,11-hexadecadienyl acetate to Z,Z/Z,E-7,11-hexadecadienyl alcohol released from the sustained release formulation of the control composition through the barrier layer.

There were provided three polyethylene tubes A, B and C each having an inner diameter of 0.8 mm, an outer diameter of 1.6 mm and a length of 200 mm. Z,Z/Z,E-7,11-hexadecadienyl acetate (0.08 g; Z,Z:Z,E=50:50) was introduced into the tube A, Z,Z/Z,E-7,11-hexadecadienyl alcohol (0.08 g; Z,Z:Z,E=50:50) was introduced into the tube B and a 98:2 mixture of the foregoing acetate and alcohol (0.08 g) was introduced into the tube C and both ends of these tubes were sealed. The release rate of each component was examined over 20 days at a temperature of 40° C. and a wind velocity of 0.5 m/sec. The results thus obtained are summarized in the following Table 1. In Table 1, HDDA and HDDOL represent Z,Z/Z,E-7,11-hexadecadienyl acetate and Z,Z/Z,E-7,11-hexadecadienyl alcohol respectively.

TABLE 1

| Polyethylene Tube | Component added to Tube (Mixing Ratio) | Release Rate of Each Component (μg/day) |
| --- | --- | --- |
| A | HDDA (100%) | 816 |
| B | HDDOL (100%) | 0 |
| C | HDDA (98%) | 810 |
|   | HDDOL (2%) | 8* |

*HDDOL in the tube C was not released during initial 3 days.

The results of the foregoing experiments clearly indicate that Z,Z/Z,E-7,11-hexadecadienyl acetate can easily emit through the polyethylene barrier layer when it is used alone (tube A), that Z,Z/Z,E-7,11-hexadecadienyl alcohol cannot easily emit through the polyethylene barrier layer when it is used alone (tube B) and that when these two components are used in combination (tube C), the release rate of Z,Z/Z,E-7,11-hexadecadienyl alcohol is improved as compared with the case wherein it is used alone (tube B). In other words, the alcohol derivative and the acetate derivative have the same groups and the emission rate of the former through the barrier layer is substantially lower than the emission rate of the latter therethrough, but the alcohol derivative in the control composition which comprises these alcohol and acetate derivatives in combination exhibits a emission rate through the barrier greater than that observed when the alcohol derivative is used alone.

Further, there were provided a polyethylene tube I having an inner diameter of 0.8 mm, an outer diameter of 1.6 mm and a length of 200 mm, a polyethylene tube II having an inner diameter of 0.8 mm, an outer diameter of 1.3 mm and a length of 200 mm and a polyethylene tube III having an inner diameter of 0.8 mm, an outer diameter of 2.0 mm and a length of 200 mm.

99:1, 98:2, 95:5, 90:10, 85:15, 80:20, 70:30, 65:35 and 50:50 mixtures of the foregoing acetate and alcohol (0.08 g) were introduced into each tube and both ends of these tubes were sealed.

Z,Z/Z,E-7,11-hexadecadienyl acetate and Z,Z/Z,E- 7,11-hexadecadienyl alcohol released from these formulations were examined by the gas chromatography technique at a temperature of 40° C. and a wind velocity of 0.5 m/sec. The results thus obtained are summarized in the graph shown in FIG. 1. An area (A) in the graph shown in FIG. 1 shows a range of preferable release ratio for mating disruption.

The results of the foregoing experiments clearly indicate that it is necessary, when a polyethylene tube is used, to determine the composition to be loaded and the thickness of the barrier in order to release the acetate derivative and the alcohol derivative in a predetermined release weight ratio.

Figure 2:
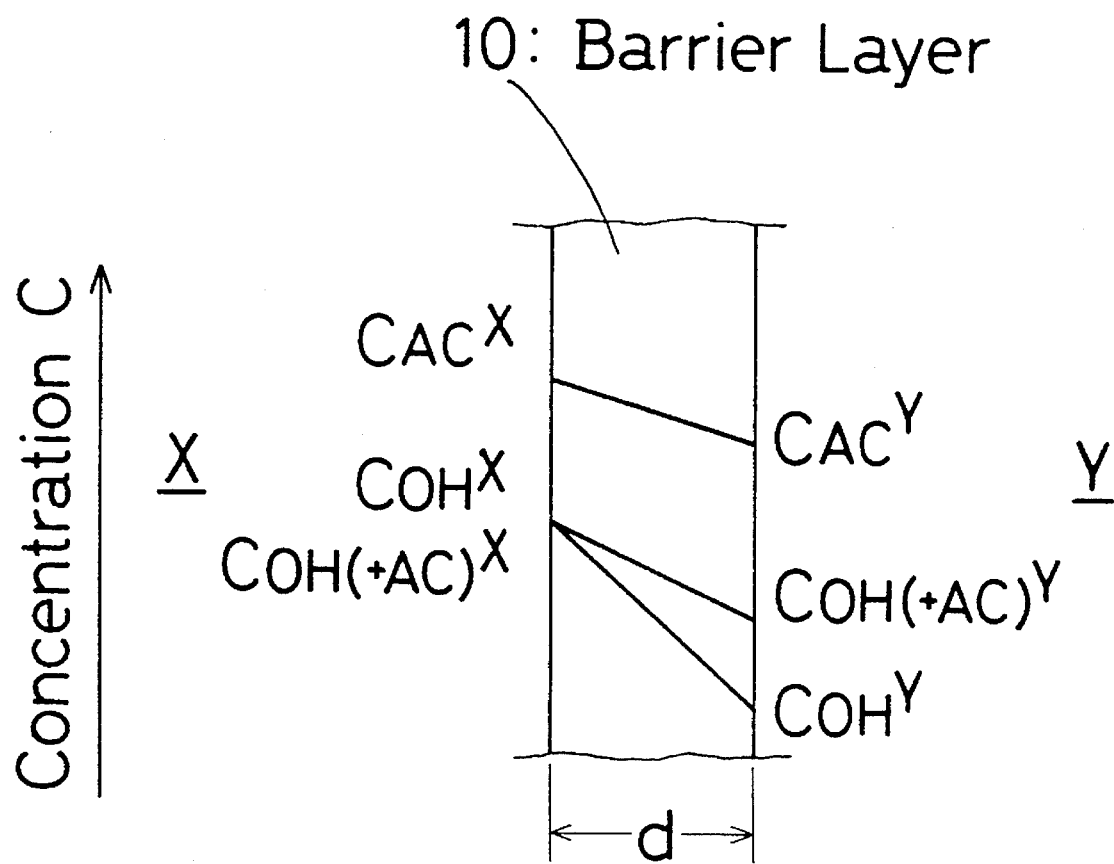
FIG. 2 is a schematic diagram for illustrating the concentration gradients of the components of the control composition observed within a barrier layer.

As seen from the results of the foregoing experiments, the following method permits the release of the acetate and alcohol derivatives present in the control composition in a predetermined weight ratio. The method will be explained with reference to a schematic diagram shown in FIG. 2. In FIG. 2, the reference numeral 10 represents a barrier layer, X represents the side of the barrier layer 10 at which the control composition is present (i.e., the interior of the tube), Y represents the side of the layer 10 at which the air is present (i.e., the outside the tube) and d represents the thickness of the barrier layer 10.

The component having a high rate of permeation (emission rate) through the barrier layer 10 such as the acetate derivative shows a small concentration gradient: $(C_{AC}^X - C_{AC}^Y)/d$ within the barrier layer 10, while that having a low permeation rate such as the alcohol derivative shows a high concentration gradient: $(C_{OH}^X - C_{OH}^Y)/d$ within the barrier layer 10. However, when the alcohol and acetate derivatives are mixed, the molecules of the acetate derivative induce plasticization of the barrier layer 10. This leads to an increase in the permeation rate of the alcohol derivative and hence the reduction of the concentration gradient: $(C_{OH(+AC)}^X - C_{OH(+AC)}^Y)/d$ of the alcohol derivative. Since the concentration gradient of the alcohol derivative is greater than that of the acetate derivative, the concentration of the alcohol derivative on the side of the air Y is greatly influenced by the thickness d of the barrier layer 10. Thus, the thickness of the barrier layer 10 should be determined in proportion to the amount of the acetate derivative released and the relative amount of the alcohol derivative (i.e., the weight ratio of the acetate derivative to the alcohol derivative) should be determined on the basis of the thickness of the barrier layer 10 in order to release, in a predetermined weight ratio, the acetate and alcohol derivatives in the form of a sustained release formulation obtained by loading the control composition in the barrier layer 10. If the thickness d of the barrier layer 10 is thin, the weight ratio of the alcohol derivative to the acetate derivative released through the barrier layer is approximately equal to the mixing weight ratio of the alcohol derivative to the acetate derivative, while if the thickness d of the barrier layer 10 is thick, the weight ratio of the alcohol derivative to the acetate derivative released through the barrier layer is lower than the mixing weight ratio of the alcohol derivative to the acetate derivative present in the control composition.

As will be described in the following Examples 1 to 7, various kinds of sustained release formulations of the control composition provided with a barrier layer were prepared while taking into consideration of the foregoing concepts and practically used in a cotton field to examine the communication-disturbing effect thereof on pink bollworm.

EXAMPLES 1 TO 7

Control compositions comprising the sex pheromone of pink bollworm, i.e., Z,Z/Z,E-7,11-hexadecadienyl acetate (HDDA in Table 2) and Z,Z/Z,E-7,11-hexadecadienyl alcohol (HDDOL in Table 2) in weight ratios listed in the following Table 2 were introduced into polyethylene tubes each having an inner diameter of 0.8 mm, an outer diameter of 1.6 mm and a length of 200 mm and then both ends of each tube were sealed to give sustained release formulations. The amounts of Z,Z/Z,E-7,11-hexadecadienyl acetate and Z,Z/Z,E-7,11-hexadecadienyl alcohol released from each sustained release formulation at a temperature of 40° C. and a wind velocity of 0.5 m/sec were determined by the gas chromatography technique. The results thus obtained are summarized in Table 2.

COMPARATIVE EXAMPLES 1 to 4

The same experiments performed in Examples 1 to 7 were carried out using the control compositions whose release weight ratio of Z,Z/Z,E-7,11-hexadecadienyl acetate to Z,Z/Z,E-7,11-hexadecadienyl alcohol was beyond the range of from 99.2:0.8 to 90:10 defined above by way of comparison.

The sustained release formulations prepared in Examples 1 to 7 and Comparative Examples 1 to 4 each was applied in a cotton field to evaluate the communication-disturbing effect thereof. The effect observed when the sex pheromone was not used at all was likewise evaluated (Comparative Example 5) by way of comparison. A cotton field was divided into 12 sections each having an area of 10 a and each formulation was uniformly distributed in each section at a density of 30 formulations/10 a by fastening them to the stems of cotton plants with strings. The copulation rate for each section was determined by fastening the alae of virgin female pink bollworms (20 each) to cotton plants with fine yarns at the center of each section to determine the number of the copulated female bollworms. The results are listed in Table 2. The data listed in Table 2 clearly indicate that the formulations of Examples 1 to 7 show excellent communication-disturbing effect.

TABLE 2

| Ex. No. | Component | Ratio Z,Z/Z,E(%) | Mixing Ratio(wt %) | Release Ratio (wt %) | Rate of Copulation |
|---|---|---|---|---|---|
| 1 | HDDA | 50:50 | 98.5 | 99.2 | 15 (%) |
|   | HDDOL | 50:50 | 1.5 | 0.8 |  |
| 2 | HDDA | 50:50 | 98.3 | 99.0 | 5 (%) |
|   | HDDOL | 50:50 | 1.7 | 1.0 |  |
| 3 | HDDA | 50:50 | 94.8 | 97.0 | 0 (%) |
|   | HDDOL | 50:50 | 5.2 | 3.0 |  |
| 4 | HDDA | 50:50 | 91.3 | 95.0 | 5 (%) |
|   | HDDOL | 50:50 | 8.7 | 5.0 |  |
| 5 | HDDA | 50:50 | 82.5 | 90.0 | 20 (%) |
|   | HDDOL | 50:50 | 17.5 | 10.0 |  |
| 6 | HDDA | 68:32 | 94.8 | 97.0 | 5 (%) |
|   | HDDOL | 68:32 | 5.2 | 3.0 |  |
| 7 | HDDA | 33:67 | 94.8 | 97.0 | 15 (%) |
|   | HDDOL | 33:67 | 5.2 | 3.0 |  |
| 1* | HDDA | 50:50 | 100 | 100 | 60 (%) |
| 2* | HDDA | 50:50 | 99.0 | 99.5 | 40 (%) |
|   | HDDOL | 50:50 | 1.0 | 0.5 |  |
| 3* | HDDA | 50:50 | 73.0 | 85.0 | 55 (%) |
|   | HDDOL | 50:50 | 27.0 | 15.0 |  |
| 4* | HDDA | 25:75 | 94.8 | 97.0 | 30 (%) |
|   | HDDOL | 25:75 | 5.2 | 3.0 |  |
| 5* | none | — | — | — | 95 (%) |

*Comparative Example.

What is claimed is:
1. A method for controlling pink bollworm in a field through disturbing the male-female communication thereof comprising introducing a mixture of Z,Z/Z,E-7,11-hexadecadienyl acetate wherein the ratio of Z,Z to Z,E acetate is from 3:7 to 7:3 and Z,Z/Z,E-7,11-hexadecadienyl alcohol wherein the ratio of Z,Z to Z,E alcohol is from 3:7 to 7:3 into a polyethylene container; sealing the container having an average thickness ranging from 0.2 mm to 0.8 mm and placing the container in the field to release the mixture, the weight ratio of acetate to alcohol in the mixture being effective to result in a released weight ratio of acetate to alcohol ranging from 99.2:0.8 to 90:10.

2. The method of claim 1 wherein the mixture is released at rate ranging from 4 to 80 mg/hr/hectare of field.

3. The method of claim 1 wherein the mixture introduced to the container is effective to release a weight ratio of acetate to alcohol in the range from 98.7:13 to 95:5.

4. The method of claim 1 wherein the container is a tube.

5. The method of claim 1 wherein the container is a bag.

6. The method of claim 1 wherein the container is a capsule.

7. The method of claim 1 wherein the container is an ampule.

* * * * *